(12) United States Patent
Svensson et al.

(10) Patent No.: US 6,468,807 B1
(45) Date of Patent: Oct. 22, 2002

(54) MIXING METHOD

(75) Inventors: Johnny Svensson, Ängelholm (SE); Bertil Nilsson, Bjärred (SE); Per Olsson, Munka Ljungby (SE); Lars Jansson, Ängelholm (SE)

(73) Assignee: Hemocue AB, Ängelholm (SE)

( * ) Notice: Subject to any disclaimer, the term of this patent is extended or adjusted under 35 U.S.C. 154(b) by 26 days.

(21) Appl. No.: 09/612,273

(22) Filed: Jul. 7, 2000

Related U.S. Application Data

(63) Continuation of application No. PCT/SE99/00046, filed on Jan. 14, 1999.

(30) Foreign Application Priority Data

Jan. 14, 1998 (SE) ................................................ 9800070

(51) Int. Cl.⁷ .............................................. G01N 33/543
(52) U.S. Cl. ........................ 436/518; 356/337; 356/339; 356/426; 356/427; 356/428; 356/441; 356/246; 422/58; 422/101; 422/102; 435/7.1; 435/286.7; 435/288.3; 435/288.5; 435/288.7; 436/164; 436/165; 436/514; 436/827
(58) Field of Search ................................ 356/337, 339, 356/426, 427, 428, 441, 246; 422/58, 101, 102; 435/286.7, 288.3, 288.5, 288.7, 7.1; 436/164, 165, 514, 518, 827

(56) References Cited

U.S. PATENT DOCUMENTS

| | | | |
|---|---|---|---|
| 4,088,448 A | 5/1978 | Lija et al. | |
| 4,936,687 A | 6/1990 | Lija et al. | |
| 5,658,723 A | 8/1997 | Oberhardt | |

FOREIGN PATENT DOCUMENTS

| | | |
|---|---|---|
| DE | 107783 | 8/1974 |
| EP | 0018435 | 11/1980 |
| EP | 0075605 | 4/1983 |
| EP | 0 075 605 | 4/1983 |
| EP | 0287883 | 10/1988 |
| EP | 0803288 | 10/1997 |
| WO | 96/33399 | 10/1996 |

*Primary Examiner*—Christopher L. Chin
(74) *Attorney, Agent, or Firm*—Burns, Doane, Swecker & Mathis, LLP

(57) ABSTRACT

The invention relates to a method for carrying out mixing in a thin liquid layer, which is arranged between essentially parallel walls at a capillary distance from each other. The mixing is carried out by subjecting the walls to a motion essentially in the plane of the liquid layer, balancing the motion against the capillary force exerted by the walls on the liquid, and selecting the interface between the liquid layer and the surrounding medium so that it functions as an elastic membrane. The invention also concerns a cuvette which is designed for mixing according to the method.

21 Claims, 1 Drawing Sheet

MIXING METHOD

This is a continuation of International Application No. PCT/SE99/00046, filed Jan. 14, 1999 that designates the United States and claims priority for Swedish Application No. 9800070-6, filed Jan. 14, 1998.

FIELD OF THE INVENTION

The present invention relates to a method for carrying out mixing in thin liquid layers. More specifically, the invention concerns a method for carrying out mixing in disposable devices to permit quantitative and qualitative analyses. The invention also concerns a method for performing such analyses as well as devices which are suited for use when performing the analyses.

BACKGROUND ART

Disposable devices, so-called microcuvettes, are disclosed in, for instance, Patent Publications EP-469 097 and WO 96/33399. These microcuvettes are intended for sampling of liquid, such as blood, mixing of the liquid sample with a reagent and direct optical analysis of the sample mixed with the reagent. The micro-cuvette comprises a body with a cavity which contains a measuring area. The cavity communicates with the surroundings outside the body through an inlet. Moreover, the cavity has a predetermined volume and is designed in such manner that the sample can enter by capillary force. A dry reagent is applied to the surface of the measuring cavity. Microcuvettes of this type have been commercially successful to a considerable extent and are currently used for quantitative determination of, for instance, haemoglobin and glucose in whole blood. An important factor which has contributed to this success is that the time from sampling to response is very short. One reason for this period of time being very short is that the reagent compositions that are used for determination of haemoglobin and glucose are readily soluble in the small amount of blood that is sucked into the capillary cavity of the microcuvette, which results in a mixing with uniform distribution of the reagent components practically immediately. However, it has been found that these prior-art microcuvettes are less suitable for determining components that require reagents, which are not readily soluble and/or in which diffusion problems exist and which therefore require a comparatively long period of time for dissolution and reaction.

A method, which has been developed specifically for mixing a liquid and a reagent in the thin capillary layers that exist in the microcuvettes, has been suggested in U.S. Pat. No. 4,936,687. In this method, use is made of small magnetic particles as means to accomplish the mixing, and the actual mixing operation is carried out by using outer magnets, which are specially designed and arranged in a special manner and operated in a predetermined fashion. After the mixing procedure, the magnetic particles are separated from that part of the sample which is to be analysed. Although this method functions well for certain types of liquids/reagents, it is not particularly attractive from an industrial and commercial point of view since special arrangements and designs of magnets are necessary. The use of fine magnetic particles and the separation of these particles after the mixing step also require time and work, which makes the method complicated and comparatively expensive. Moreover, there is a risk of chemical obstruction, caused by the magnetic particles, of both samples and reagents.

Furthermore, EP 75 605 discloses a method for mixing in capillary liquid layers. According to this method, the mixing is carried out in a reaction vessel, which comprises two parallel plates which are movable relative to and towards each other. Just a few microlitres of reagent and sample are applied, when filling the reaction vessel, to particular adhesion surfaces or in various positions within an adhesive surface of the plates, and mixing of sample and reagent is carried out by moving the plates towards each other and perpendicular to the liquid layer formed by the sample and the reagent. This prior-art method thus requires that both sample and reagent be present in the form of liquid, which makes it easier to carry out the mixing compared with the above microcuvettes with a dry reagent which besides is difficult to dissolve. This type of mixing, i.e. where the liquid layer is made to move perpendicular to the plane of the layer, has been tested to achieve mixing in microcuvettes of the above type but has not been found to be sufficiently effective.

A simple and effective method for mixing of liquid and reagent in thin capillary layers, which is also suitable to accelerate the dissolution of less soluble reagents, would increase the number of determinations that can be carried out in both microcuvettes and devices of the same fundamental design as the microcuvettes. As a result, analyses which up to now could not be performed or for which there has previously been no interest in connection with disposable devices for essentially simultaneous sampling and analysis and with capillary drawing in of the sample could also be attractive.

SUMMARY OF THE INVENTION

According to the invention, mixing is carried out in a capillary liquid layer arranged between two essentially plane-parallel walls by the walls, which are essentially immovable relative to each other, being subjected to a motion essentially in the plane of the liquid layer, balancing the motion against the capillary force exerted by the walls on the liquid and selecting the interface between the liquid layer and the surrounding medium so that it functions as an elastic membrane. The invention also concerns a disposable device intended for use when carrying out the method and especially in sampling and analysis.

This method is well suited to achieve more rapid dissolution of certain dry reagents which are relatively difficult to dissolve, and more efficient mixing of sample and reagent in the thin liquid layers that are present in disposable devices or microcuvettes of the above type. In principle, however, the mixing method can be applied to all liquids in the form of thin layers between essentially parallel walls which are arranged at a capillary distance from each other.

DETAILED DESCRIPTION OF THE INVENTION

The capillary force depends on the type of material of the walls, the type of sample including additives, if any, such as reagents, and the distance between the walls. The frequency and amplitude parameters of the motion must be balanced against the capillary force that is present in the individual case, and these parameters must be sufficient to provide mixing without any risk that part of the liquid escapes from the microcuvette, which may happen if the frequency/amplitude is too high.

The upper limit of the length of the elastic membrane, i.e. of the interface of the sample towards the surrounding medium, such as air, is present in the case where the volume of the liquid sample is only limited by the parallel walls and is not enclosed in a cavity. The lower limit is determined experimentally on the basis of sample liquid, reagent, suitable beat frequency, cavity depth etc.

When the correct conditions for the motion are present, the interface serves as an elastic membrane which forces the chemical compounds in the sample liquid and a reagent composition, if any, which is dissolved or being dissolved, to move with the liquid motion, which results in a mixing of sample liquid and reagent in the thin liquid layer.

According to the present invention, the mixing is thus carried out by making a device with a liquid layer of a liquid sample and reagent move essentially in the plane of the liquid layer during a period of time and at a speed which are sufficient to accomplish the desired mixing. The motion can be rotating but a reciprocating motion is preferred. Any combination of these motions can also be used. As mentioned above, an important feature of the new mixing method is that the motion is balanced against the capillary force so that the liquid sample does not flow out of the device. The capillary force is determined by the type of sample and the material of the walls of the device, and the balancing operation is preferably made experimentally. As indicated above, it is a critical feature that the interface between the sample and the surroundings is selected so that this interface can serve as an elastic membrane. The interface between sample and air in the inlet of the disposable device or microcuvette will serve as an elastic membrane only on the condition that the length of this inlet is sufficient or if the device contains at least one more cavity, which is essentially non-capillary and can form a further elastic membrane. In the latter case, the inlet of the cuvette need not be greater than the distance between essentially plane-parallel walls which define the measuring cavity, while in the former case, i.e. when the volume of the sample liquid only forms a continuous interface (a continuous membrane) against the surrounding medium (air), the length of the inlet should be at least 5, preferably at least 10 times greater than the depth of the liquid layer in the measuring cavity.

A microcuvette which is suited for mixing according to the invention, comprises a body with a measuring cavity which is defined by two essentially parallel surfaces, which define an optical path and are arranged at a predetermined distance from each other. The measuring cavity has a predetermined volume and a capillary inlet connects the cavity with the surroundings outside the body. Under the action of capillary force, the sample is drawn into the measuring cavity through the inlet. A predetermined amount of dry reagent is arranged in the measuring cavity, e.g. applied to the surface of the cavity. The walls of the microcuvette are preferably transparent and non-elastic. The volume of the cuvette may vary between 0.1 $\mu$ and 1 ml and the thickness of the thin layer may vary between 0.01 and 2.00 mm, and preferably between 0.1 and 1.0 mm. The distance between the walls at the inlet or opening of the cuvette can preferably be between 0.01 and 1 mm and is preferably greater than the distance between the walls in the measuring cavity.

The mixing method according to the present invention is, of course, also suited for mixing in devices which are not intended to be used for optical, for instance, turbidimetric or nephelometric, measurement, but it is generally applicable to mixing in thin liquid layers. Examples of other types of measurements are radioactive measurements, in which optical path length and transparent walls are not required. In general terms, it may be said that the sampling device is designed in respect of the analysis for which it is intended, and the sampling devices have the common feature that under the action of capillary force the sample can be drawn into a capillary cavity and mixing of sample and reagent occurs in a capillary liquid layer.

The method for mixing according to the invention is particularly applicable when it is desirable to perform essentially simultaneous sampling and quantitative determination of a component in a liquid sample in a capillary disposable device, such as a microcuvette. This sampling and determination comprise the steps of inserting the sample containing the component to be determined into a disposable device, which contains at least a dry reagent for the component and into which the sample is drawable under the action of capillary force through an inlet in a capillary cavity, which is defined by two essentially plane-parallel walls, subjecting the device to a motion to accelerate the dissolution of the reagent and mixing in the thin liquid layer of reagent and sample, said layer being formed between the plane-parallel walls which define the cavity, the motion occurring essentially in the plane of the liquid layer and being balanced against the capillary force exerted by the walls on the liquid layer, and the interface between the liquid layer and the surrounding medium being selected so that it functions as an elastic membrane, and subjecting the resulting mixture to measurement in a measuring area.

An important feature of the mixing method according to the invention is that the motion occurs essentially in the plane of the liquid layer, i.e. that the motion, which preferably can be a reciprocating vibration at an experimentally determined frequency and amplitude, occurs essentially in parallel with the principal plane of the capillary cavity. Minor deviations from the principal plane can be tolerated, but deviations above 20° from this plane have been found to result in a clearly deteriorated mixing effect.

Even if any type of reagent can be applied in the cuvette, special advantages are achieved when using reagents which are comparatively difficult to dissolve, such as proteins and carbohydrates.

The components which are particularly interesting to analyse in the inventive measuring method are macromolecular compounds such as proteins, for instance albumin or other proteins, e.g. CRP (C-Reactive Protein), with which turbidimetrically measurable antigen-antibody aggregates can be produced. The application of the present invention may also comprise non-protein-based antigens, such as polysaccharides. The inventive principle can be applied in many contexts where turbidimetric quantification of an analyte can occur. In such optical measurement in a microcuvette, the walls in the measuring area are arranged with a predetermined optical path length.

An example of an analysis where mixing in a microcuvette has extensive practical use, are the analyses which are based on antigen-antibody reactions, such as in determination of $\mu$ albumin in urine, in which antibodies against human albumin are made to react with albumin in a urine sample. A predetermined amount of antialbumin-anti-bodies together with PEG 6000 is supplied to the cavity of the cuvette and dried. When the sample enters the cuvette cavity, which has a predetermined volume and gap width, the reagent is dissolved if the cuvette is made to vibrate at a frequency of 60 beats/s. Albumin which is present in the urine sample, reacts with the dissolved antibodies and forms aggregates, which cause turbidity that can be measured spectrophotometrically at 470 nm and that is proportional to the concentration of albumin in the sample. Correspondingly, analyses can be performed on albumin or some other protein in blood or plasma. A mixing according to the present invention, which preferably is carried out in a spectrophotometer of the type disclosed in Swedish Patent Application 9800072-2, is an important condition for a quick and reproducible response.

According to a preferred embodiment, the essentially non-capillary cavity is arranged adjacent to the capillary measuring cavity containing the dry reagent and is arranged essentially in alignment with the inlet and the measuring cavity. When the liquid sample in this embodiment is drawn into the cuvette and mixed according to the invention, the liquid in the cavity and the medium, usually air, which is present in the non-capillary cavity, form a separate interface which also serves as an elastic membrane.

Inventive measuring cuvettes are illustrated in the accompanying drawings, in which FIG. 1 is a perspective view of a microcuvette, FIG. 2 is a cross-sectional view of the microcuvette in FIG. 1

Figure 1:
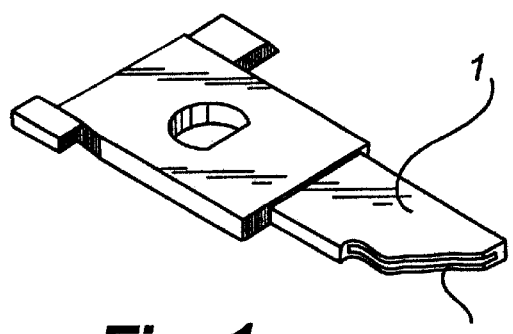
Figure 2:
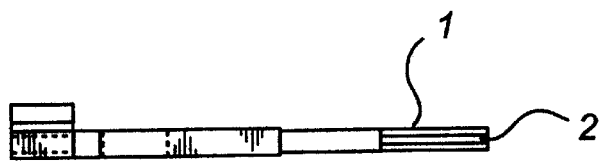

In FIG. 1, 1 designates the microcuvette and 2 the capillary inlet, which, when the sample has been drawn the cuvette, forms an elastic membrane against the surrounding air.

Figure 3:
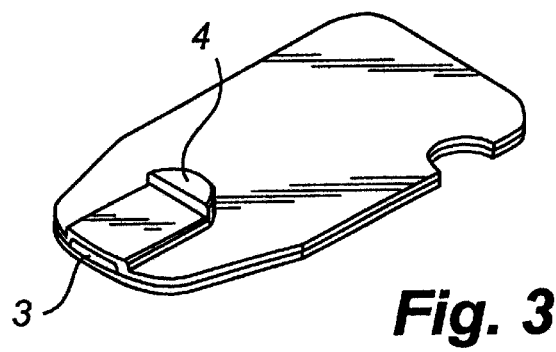
FIG. 3 is a perspective view of a microcuvette with two cavities.
Figure 4:
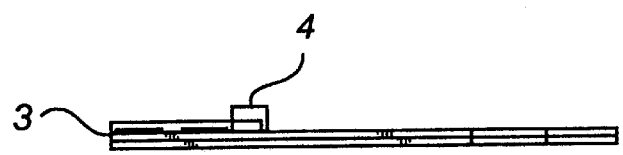
FIG. 4 is a cross-sectional view of the microcuvette in FIG. 3.

In a corresponding manner, two elastic membranes form against air in the microcuvette illustrated in FIGS. 3 and 4, in which 3 indicates the capillary inlet and 4 a cavity of a greater depth, which cavity is essentialy non-capillary.

The agitation according to the invention can be exemplified as follows.

The agitation was studied as a function of cavity depth and beat frequency. Cuvettes having the same design of the cavity were used.

| Cavity Depth | Beat Frequency (beats/s) | Comments |
| --- | --- | --- |
| 150 µm | 60 | no agitation |
| 130 µm in measuring eye/400 µm outside | 60 | agitation in 400 µm no agitation in 130 µm |
| 130 µm in measuring eye/400 µm outside | 30 | no agitation |
| 300 µm | 60 | no agitation |
| 300 µm | 30 | no agitation |
| 500 µm | 60 | good agitation |
| 500 µm | 30 | no agitation |
| 700 µm | 60 | good agitation |

The results show that the agitation is dependent on both beat frequency and cavity depth. Thus, good agitation is obtained in a 400-µm-deep cuvette at 60 beats/s but not at 30 beats/s. If the depth of the cavity decreases, no agitation occurs.

What is claimed is:

1. A method for essentially simultaneous sampling and quantitative determination of a component in a liquid sample, comprising the steps of:

inserting the liquid sample containing the component to be determined into a disposable device, which contains at least a dry reagent for determining the component and into which the sample is drawable under the action of capillary force through an inlet in a capillary cavity, wherein the capillary cavity is defined by two essentially plane-parallel walls, said inlet connecting the cavity with a surrounding medium outside the disposable device, forming a thin liquid layer in the capillary cavity, said layer being formed between the plane-parallel walls which define the capillary cavity, subjecting the disposable device to a motion essentially in the plane of the thin liquid layer to accelerate dissolution of the reagent and mixing in the thin liquid layer of the dry reagent and the liquid sample, and balancing the motion against the capillary force exerted by the walls on the liquid sample such that the liquid sample does not flow out of the disposable device, forming an interface between the thin liquid layer and the surrounding medium so that it functions as an elastic membrane, and subjecting a resulting mixture of the reagent and liquid sample to a measurement so as to determine the component in the liquid sample.

2. A method as claimed in claim 1, wherein the component is a macromolecular compound.

3. A method as claimed in claim 2, wherein, in mixing, the reagent and the macromolecular compound form an aggregate which consists of an antibody-antigen complex or a lectin-carbohydrate complex.

4. A method as claimed in claim 3, wherein the motion is an essentially reciprocating motion.

5. A method as claimed in claim 2, wherein the macromolecular compound consists of a plasma protein.

6. A method as claimed in claim 5, wherein the plasma protein comprises albumin or a C-Reactive Protein (CRP).

7. A method as claimed in claim 2, wherein the motion is an essentially reciprocating motion.

8. A method as claimed in claim 1, wherein the reagent is an antibody or a lectin.

9. A method as claimed in claim 8, wherein the motion is an essentially reciprocating motion.

10. A method as claimed in claim 1, wherein the motion is an essentially reciprocating motion.

11. A method as claimed in claim 1, wherein the measurement is an optical measurement.

12. A method as claimed in claim 11, wherein the optical measurement is a turbidimetric or nephelometric measurement.

13. A method as claimed in claim 2, wherein the macromolecular compound comprises a protein or a carbohydrate.

14. A method for essentially simultaneous sampling and quantitative determination of a component in a liquid sample, comprising the steps of:

inserting the liquid sample including the component to be determined into a disposable device, wherein the disposable device contains at least a dry reagent enabling quantitative determination of the component and the disposable device includes a capillary cavity having an inlet, wherein the capillary cavity is defined by two essentially plane-parallel walls the liquid sample is drawable into the disposable device under the action of capillary force through the inlet, the inlet thereby connecting the capillary cavity with a surrounding medium outside the disposable device, forming a thin liquid layer in the capillary cavity, said layer being formed between the plane-parallel walls which define the capillary cavity, subjecting the disposable device to a motion essentially in the plane of the thin liquid layer to accelerate dissolution of the reagent and mixing in the thin liquid layer of the dry reagent and the liquid sample, and balancing the motion against the capillary force exerted by the walls on the liquid sample, forming an interface between the thin liquid layer and the surrounding medium so that it functions as an elastic membrane, and subjecting a resulting mixture of the reagent and liquid sample to a measurement so as to determine the component in the liquid sample, wherein the component is a macromolecular compound.

15. A method as claimed in claim 14, wherein the macromolecular compound comprises a protein or a carbohydrate.

16. A method as claimed in claim 14, wherein the reagent is an antibody or a lectin.

17. A method as claimed in claim 14, wherein, in mixing, the reagent and the macromolecular compound form an aggregate which consists of an antibody-antigen complex or a lectin-carbohydrate complex.

18. A method as claimed in claim 14, wherein the macromolecular compound includes a plasma protein.

19. A method as claimed in claim 18, wherein the plasma protein comprises albumin or a C-Reactive Protein (CRP).

20. A method as claimed in claim 14, wherein the measurement is an optical measurement.

21. A method as claimed in claim 20, wherein the optical measurement is a turbidimetric or nephelometric measurement.

* * * * *